US012779215B2

(12) United States Patent
Seo et al.

(10) Patent No.: US 12,779,215 B2
(45) Date of Patent: Nov. 3, 2026

(54) MOUTHPIECE FOR TREATING SKIN INCLUDING INSULATION LAYER IN IMPRESSION BODY ACQUIRED IN ACCORDANCE WITH ORAL CAVITY STRUCTURE OF USER AND SKIN TREATING APPARATUS

(71) Applicant: JEISYS MEDICAL INC., Seoul (KR)

(72) Inventors: Suk Bae Seo, Seoul (KR); Ja Young Kim, Seoul (KR); Ho Joon Seo, Seoul (KR)

(73) Assignee: JEISYS MEDICAL INC., Seoul (KR)

( * ) Notice: Subject to any disclaimer, the term of this patent is extended or adjusted under 35 U.S.C. 154(b) by 921 days.

(21) Appl. No.: 17/402,052

(22) Filed: Aug. 13, 2021

(65) Prior Publication Data

US 2021/0370058 A1 Dec. 2, 2021

Related U.S. Application Data

(63) Continuation of application No. PCT/KR2020/002143, filed on Feb. 14, 2020.

(30) Foreign Application Priority Data

Feb. 14, 2019 (KR) ........................ 10-2019-0017219
Feb. 14, 2020 (KR) ........................ 10-2020-0018087

(51) Int. Cl.
*A61N 1/32* (2006.01)
*A61C 9/00* (2006.01)
(Continued)

(52) U.S. Cl.
CPC ............ *A61N 1/328* (2013.01); *A61C 9/0006* (2013.01); *A61C 9/0053* (2013.01); *A61N 1/0548* (2013.01); *A61N 1/06* (2013.01)

(58) Field of Classification Search
USPC ........................................................... 607/59
See application file for complete search history.

(56) References Cited

U.S. PATENT DOCUMENTS

| | | | | |
|---|---|---|---|---|
| 1,389,662 A * | 9/1921 | John | A61C 19/06 | 604/20 |
| 4,304,235 A * | 12/1981 | Kaufman | A61B 18/16 | 607/152 |

(Continued)

FOREIGN PATENT DOCUMENTS

| | | |
|---|---|---|
| JP | 2005-523097 A | 8/2005 |
| KR | 10-2007-0065762 A | 6/2007 |

(Continued)

OTHER PUBLICATIONS

International Search Report issued in PCT/KR2020/002143; mailed May 26, 2020.

(Continued)

*Primary Examiner* — Linda C Dvorak

(57) ABSTRACT

The inventive concept provides a mouthpiece for treating skin, in which a retaining ligament, a blood vessel, and a fiber tissue of a deep skin portion may be used as electrical passages, and which is manufactured in accordance with an oral cavity structure of a patient, and a skin treating apparatus including the mouthpiece for treating skin. The mouthpiece for treating skin includes an impression body disposed in an oral cavity of a user, and a first electrode unit disposed in the impression body, wherein the first electrode unit electrically interacts with a second electrode unit disposed outside the oral cavity of the user, and the impression body has a shape corresponding to a structure of the oral cavity of the user.

17 Claims, 20 Drawing Sheets

(51) Int. Cl.
*A61N 1/05* (2006.01)
*A61N 1/06* (2006.01)

(56) References Cited

U.S. PATENT DOCUMENTS

| | | | | |
|---|---|---|---|---|
| 5,415,544 | A * | 5/1995 | Oxman | C08L 67/04 433/48 |
| 2007/0208340 | A1* | 9/2007 | Ganz | A61B 18/1477 606/50 |
| 2008/0082090 | A1* | 4/2008 | Manstein | A61B 18/203 606/9 |
| 2008/0221642 | A1* | 9/2008 | Humayun | A61N 1/36025 607/58 |
| 2016/0038734 | A1* | 2/2016 | Nemeh | A61N 1/205 433/32 |
| 2016/0228178 | A1* | 8/2016 | Lei | A61N 1/06 |
| 2017/0215997 | A1* | 8/2017 | Martin | A61B 90/50 |
| 2020/0254243 | A1* | 8/2020 | Kim | A61N 1/0548 |
| 2020/0330753 | A1* | 10/2020 | Leonhardt | A61C 7/12 |

FOREIGN PATENT DOCUMENTS

| | | | |
|---|---|---|---|
| KR | 10-1326434 | B1 | 11/2013 |
| KR | 20150049386 | A | 5/2015 |
| KR | 10-2017-0014482 | A | 2/2017 |
| KR | 10-2017-0025060 | A | 3/2017 |
| KR | 10-2017-0108532 | A | 9/2017 |

OTHER PUBLICATIONS

Korean Intellectual Property Office, Notice of Office Action regarding Application No. 10-2020-0018087, Feb. 14, 2020.

* cited by examiner

MOUTHPIECE FOR TREATING SKIN INCLUDING INSULATION LAYER IN IMPRESSION BODY ACQUIRED IN ACCORDANCE WITH ORAL CAVITY STRUCTURE OF USER AND SKIN TREATING APPARATUS

CROSS-REFERENCE TO RELATED APPLICATIONS

The present application is a continuation of International Patent Application No. PCT/KR2020/002143, filed on Feb. 14, 2020, which is based upon and claims the benefit of priority to Korean Patent Application Nos. 10-2019-0017219 filed on Feb. 14, 2019 and 10-2020-0018087 filed on Feb. 14, 2020. The disclosures of the above-listed applications are hereby incorporated by reference herein in their entirety.

BACKGROUND

1. Technical Field

The inventive concept relates to a mouthpiece for treating skin including an insulation layer in an impression body acquired in accordance with an oral cavity structure of a user, and a skin treating apparatus.

2. Description of Related Art

In recent years, various skin treating apparatuses for removing wrinkles, restoring elasticity of skin, and removing sebum have been developed. Skin that has no wrinkles, is tight, thick, and dense, and has no elongations may provide a youthful-looking and attractive appearance.

Skin treating apparatuses that apply energy use various kinds of methods, such as a method for delivering ultrasonic waves to skin tissues (HIFU type), a method for delivering electromagnetic waves to skin tissues (in particular, a high-frequency or RF type), and irradiating laser beams to skin tissues (optical type).

In the method for delivering electromagnetic waves to skin tissues, a single radio frequency (RF) electrode or a plurality thereof penetrate into a deep skin portion, and damaged collagen or elastic fibers of the deep skin portion are removed using electrical energy and a new formation thereof is expedited. Furthermore, the method improves deposition of pigments, acne spots, and wrinkles of the skin.

Meanwhile, the skin treating apparatus using electrical energy may use direct current and alternating current power sources according to the type of the power source, and methods for using high-frequency energy of a high frequency band of an alternating current have been widely developed. Furthermore, the methods are classified into a bipolar type, in which energy flows through a portion that is proximate to an electrode, according to the electrode, and a monopolar type, in which energy between remote sites is delivered to skin tissues.

In the bipolar type, electrical energy is delivered a short distance between a plurality of electrodes, and there is a limit thereto, in that energy is concentrated in a shallow and narrow portion.

In the monopolar type, a first electrode unit 1 is used as a ground terminal and a second electrode unit 2, separately provided, is used as a power terminal to deliver electrical energy (see FIGS. 1A, 1B, 1C, 1D, and 2). Meanwhile, the second electrode unit 2 may include a plurality of needle electrodes that penetrate into a dermis to deliver electrical energy to a deep skin portion. However, this is an example of the second electrode unit 2, and the form of the second electrode unit 2 is not limited to the form of the plurality of needles.

Meanwhile, a retaining ligament connects skin and bones, and may be utilized as an electrical passage of the face as it contains a significant amount of moisture. As illustrated in FIG. 3, a central strand of the retaining ligament is branched to several strands as it goes from bone tissue (inner side) to a skin tissue (outer side). The support structure is weakened and slimmed and loses elasticity due to the effects of aging, and thus the facial portion is aged. Accordingly, as a measure, a location, at which an electrical flow that is proximate to skin and originated from a bone, may become an oral cavity mucous membrane, and FIG. 4 illustrates a picture illustrating a portion that is proximate to skin and may be used as a ground, to which electricity flows (see a dotted line area of FIG. 4).

Accordingly, when retaining ligaments, blood vessels, fiber tissues, and the like of a face are utilized as electrical passages when skin of the face is treated using electrical energy, aging and weakening of the above-described retaining ligaments and other structures are revitalized, whereby the deflection of the skin due to aging may be positively prevented.

However, according to the conventional skin treating apparatus of the monopolar type, the first electrode unit 1 contacts a predetermined body portion (for example, a back, an abdomen, and a hip; see FIG. 2) and then the first electrode unit 1 contacts a target portion. Accordingly, flows of electric currents are mainly restricted to the epidermis of the skin as the distance between the first electrode unit 1 and the second electrode unit 2 is large, and the retaining ligaments and the blood vessels of the face and fiber tissues of a deep skin portion of the face may not be utilized as electrical passages.

In order to solve this, when one of a power terminal or a ground terminal is provided in a form of a mouthpiece and disposed in an interior of a face and the remaining one of a power terminal or a ground terminal is provided in a form of a hand-piece to contact a target portion outside the face, electric currents may directly flow to the face and the retaining ligaments of the face may be utilized as electrical passages.

Moreover, when the mouthpiece is manufactured in accordance with the oral cavity structure of the patient, electrical energy may be accurately applied to a target area by reflecting the oral cavity structures that are different for each person, and the wearable performance of the user may be improved.

SUMMARY

Embodiments of the inventive concept provide a mouthpiece for treating skin, in which a retaining ligament, a blood vessel, and a fiber tissue of a deep skin portion may be used as electrical passages, and which is manufactured in accordance with an oral cavity structure of a patient and includes an insulation layer, and a skin treating apparatus including the mouthpiece for treating skin.

The technical objects of the inventive concept are not limited to the above-mentioned, and the other unmentioned technical objects will become apparent to those skilled in the art from the following description.

According to an aspect of the inventive concept, a mouthpiece for treating skin includes an impression body disposed in an oral cavity of a user, and a first electrode unit disposed in the impression body, wherein the first electrode unit electrically interacts with a second electrode unit disposed outside the oral cavity of the user, and the impression body has a shape corresponding to a structure of the oral cavity of the user.

According to another aspect of the inventive concept, a skin treating apparatus includes an electric power source unit, the mouthpiece for treating skin, which is electrically connected to the electric power source unit, and a hand-piece electrically connected to the electric power source unit, wherein the hand-piece includes a second electrode and a conductive line, and the electric power source unit applies an alternating current of a wavelength band of a high frequency to the first electrode and the second electrode.

According to another aspect of the inventive concept, a mouthpiece for treating skin including an insulation layer includes an impression body disposed in an oral cavity of a user and having a shape corresponding to a structure of the oral cavity of the user, a first electrode unit disposed in the impression body, and including a first electrode and a conductive line electrically connecting the first electrode and an external electric power source unit, and a second electrode unit disposed outside the oral cavity of the user, wherein the first electrode unit is disposed such that at least a portion thereof is exposed to an outside in correspondence to the impression body, the first electrode unit electrically interacts with the second electrode unit such that an alternating current of a wavelength band of a high frequency flows, the second electrode unit includes a plurality of needle electrodes disposed such that a tip end thereof faces the first electrode unit with an oral cavity mucous membrane being interposed therebetween and which applies electrical energy to a dermis of a deep skin portion, and an exposed surface of the first electrode is covered by the insulation layer.

According to the skin treating apparatus of the inventive concept, because the first electrode unit is disposed inside the oral cavity and the second electrode unit is disposed outside the oral cavity while skin of the face being interposed therebetween, the retaining ligament and the blood vessels of the skin of the face, the fiber tissues of the deep skin portion between cells, and the like may be utilized as electrical passages. Furthermore, because the alternating currents between the first electrode unit and the second electrode unit flow while changing their directions according to cycles, an electrical passage, in which the alternating currents flow from the inside externally through several strands branched from a central strand of the retaining ligament and are spread out from the deep skin portion, may be generated (see FIG. 3).

As a result, according to the skin treating apparatus of the inventive concept, deflection of the face due to aging of skin may be effectively improved by utilizing the retaining ligaments, the blood vessels, and inter-cell fiber tissues as electrical passages.

Furthermore, the mouthpiece for treating skin of the inventive concept may be manufactured in correspondence to the oral cavity structure of the user through an impression taking process.

As a result, when the mouthpiece for treating skin of the inventive concept is used, electrical energy may be accurately applied to a target area while reflecting the oral cavity structure of the user and the wearable performance of the user may be improved.

Furthermore, the mouthpiece for treating skin of the inventive concept is inserted into the interior of the oral cavity, and thus the ground of the mucous membrane portion is electrically stimulated whereby the tension and elasticity of the inner mucous membrane increase as new fiber tissues and elastic tissues are formed. Accordingly, because the treatment is performed while the skin of the face is maintained in a tightly spread out manner (facial tightening and tenting), the power electrode unit accurately contacts a target point and electrical energy is efficiently delivered, whereby a treatment effect may be increased. Moreover, an upper layer structure deflected into the oral cavity may be tensioned whereby the aged outer shape of the skin may be improved.

The effects of the inventive concept are not limited thereto, and other unmentioned effects of the inventive concept may be clearly appreciated by those skilled in the art from the following descriptions.

DETAILED DESCRIPTION

Figure 1A:
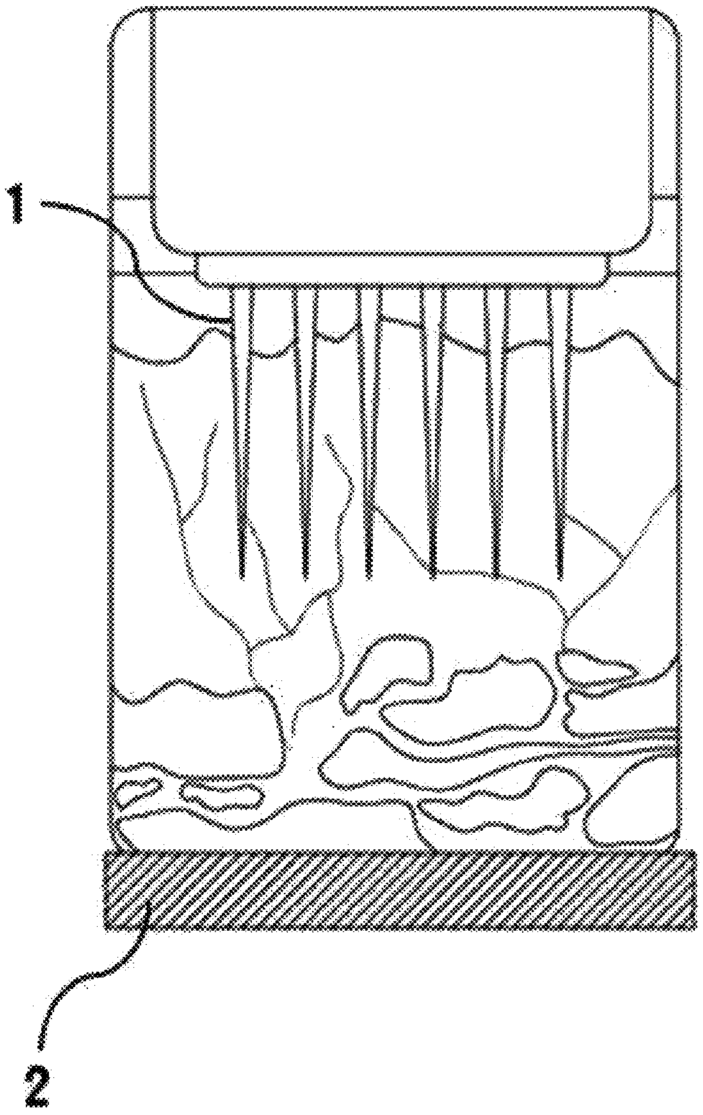
FIGS. 1A, 1B, 1C, and 1D are conceptual views illustrating a treatment process using an RF needle electrode.
Figure 1B:
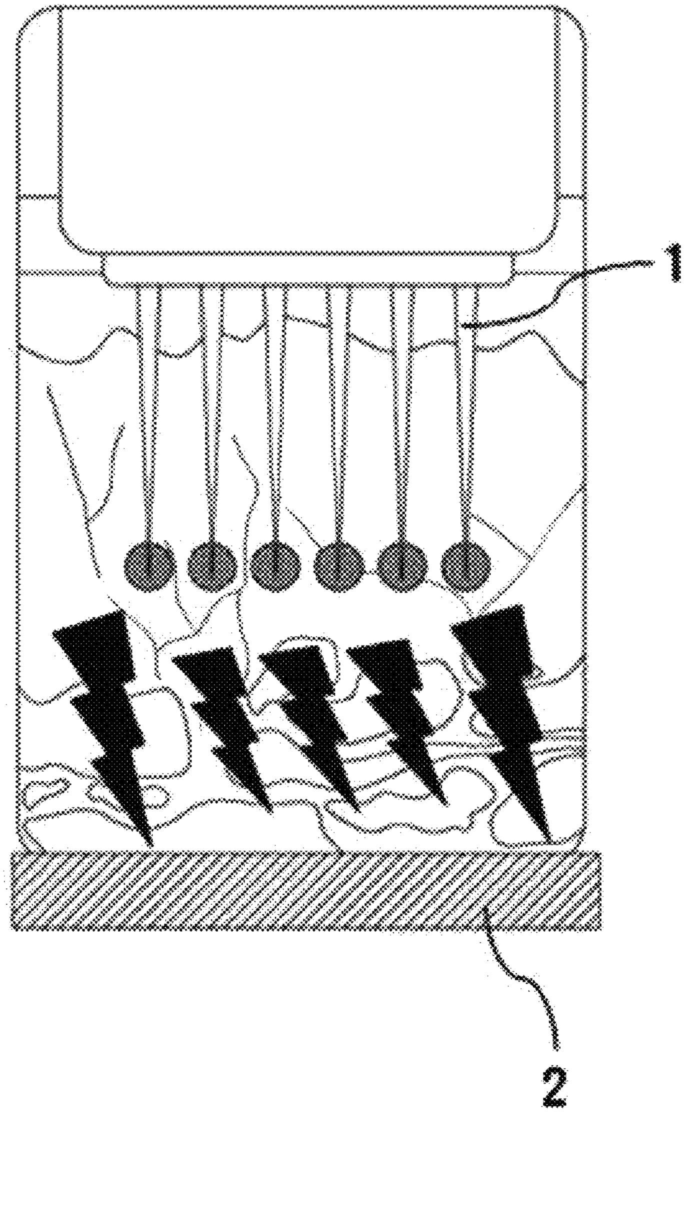
Figure 1C:
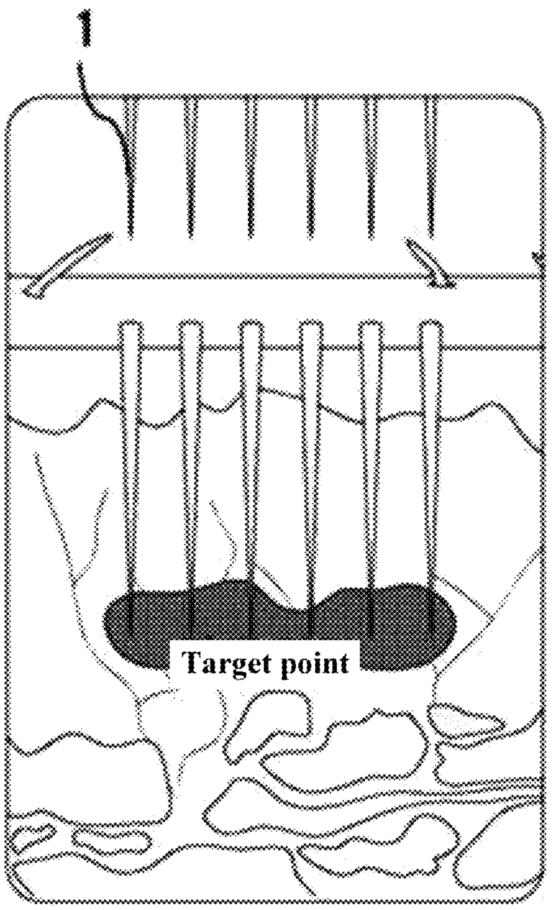
Figure 1D:
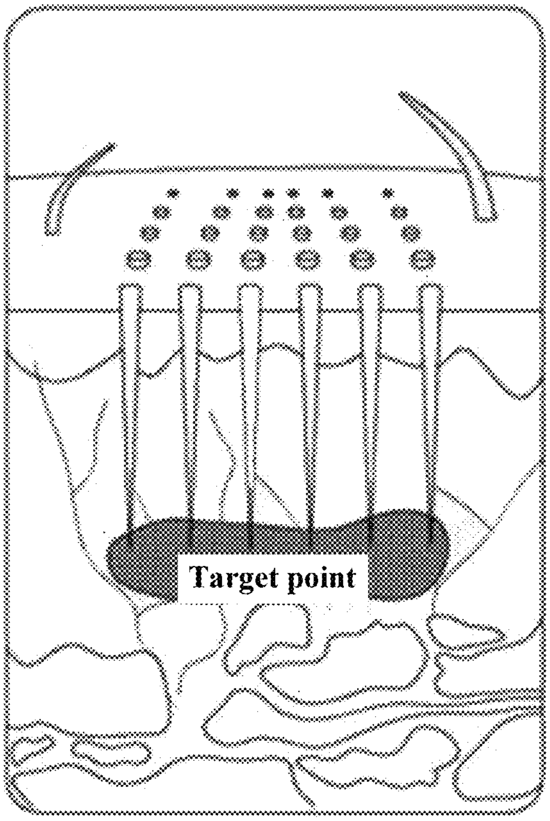
Figure 2:
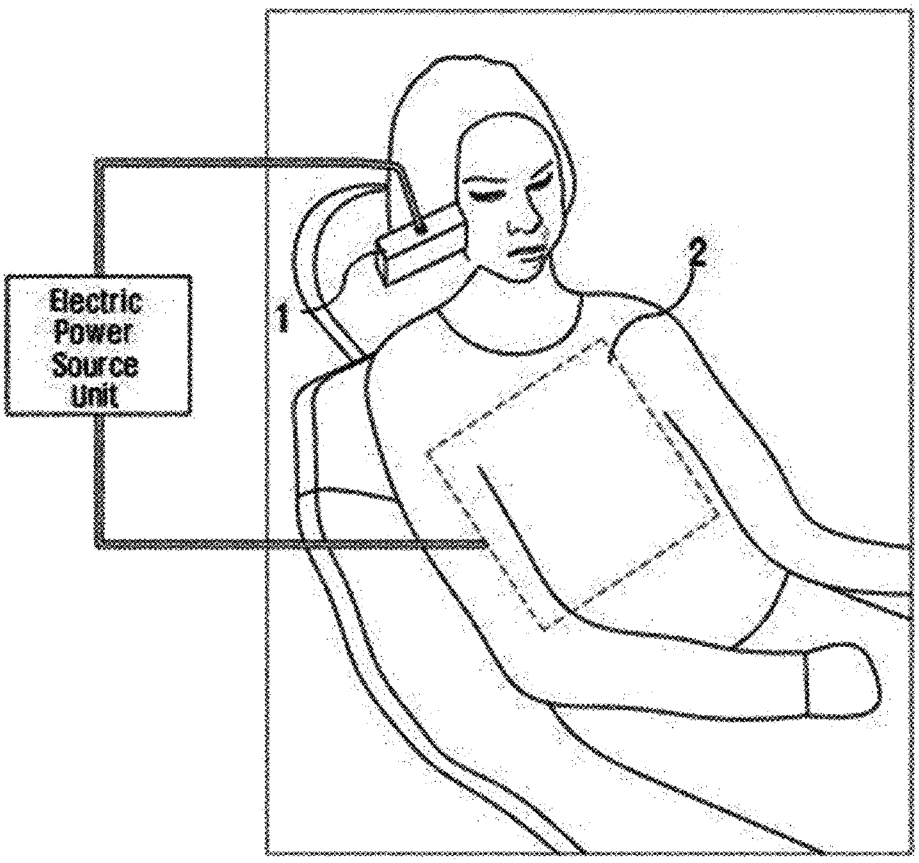
FIG. 2 is a conceptual view illustrating that a subject is treated using a conventional skin treating apparatus.

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art to which the inventive concept pertains, and the inventive concept will be defined by the scope of the claims.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals denote the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms, such as "below", "beneath", "lower", "above", and "upper", which are spatially relative may be used to easily describe a correlation between one element and other elements as illustrated in the drawings. The spatially relative terms have to be understood as terms including different directions of the elements during use or an operation, in addition to the direction illustrated in the drawings. For example, when the elements illustrated in the drawings are overturned, the elements "below" or "beneath" another element may be positioned "above" the other element. Accordingly, the term "below" or "beneath" may include "below" or "beneath" and "above." The element may be oriented in different directions, and accordingly, the spatially relative terms may be construed according to the orientation.

Figure 5:
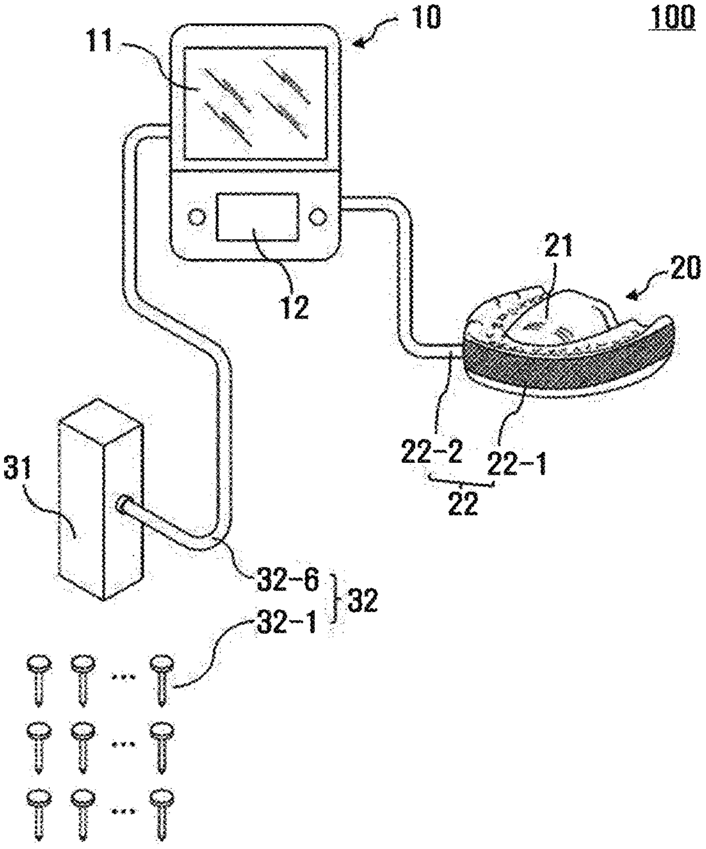
FIG. 5 is a conceptual view illustrating a skin treating apparatus of the inventive concept.
Figure 6A:
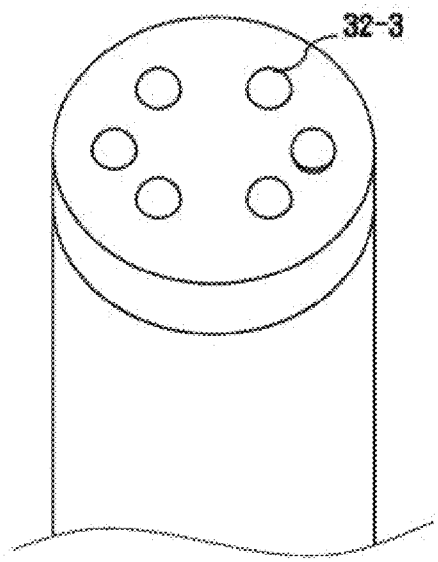
FIGS. 6A and 6B are conceptual views illustrating various embodiments of a second electrode unit of the inventive concept.
Figure 6B:
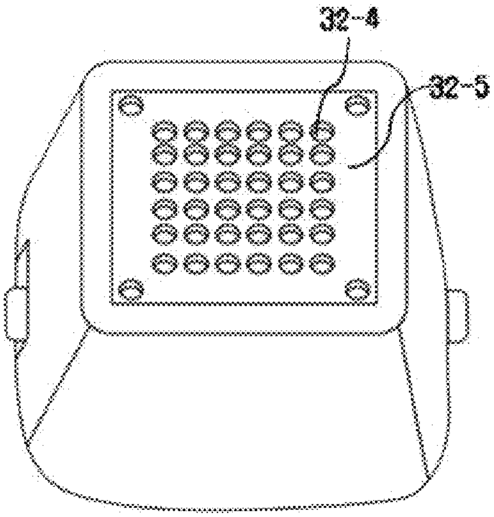
Figure 7:
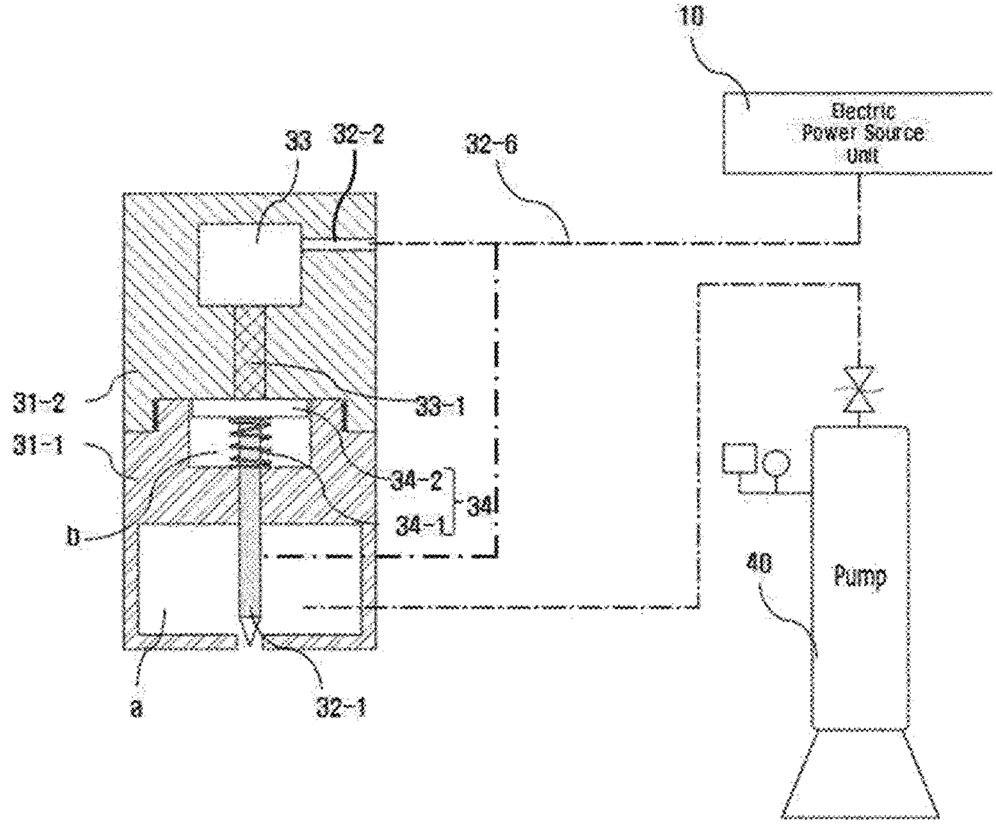
FIG. 7 is a conceptual view illustrating a cross-section and a system of a hand-piece of the inventive concept.
Figure 8A:
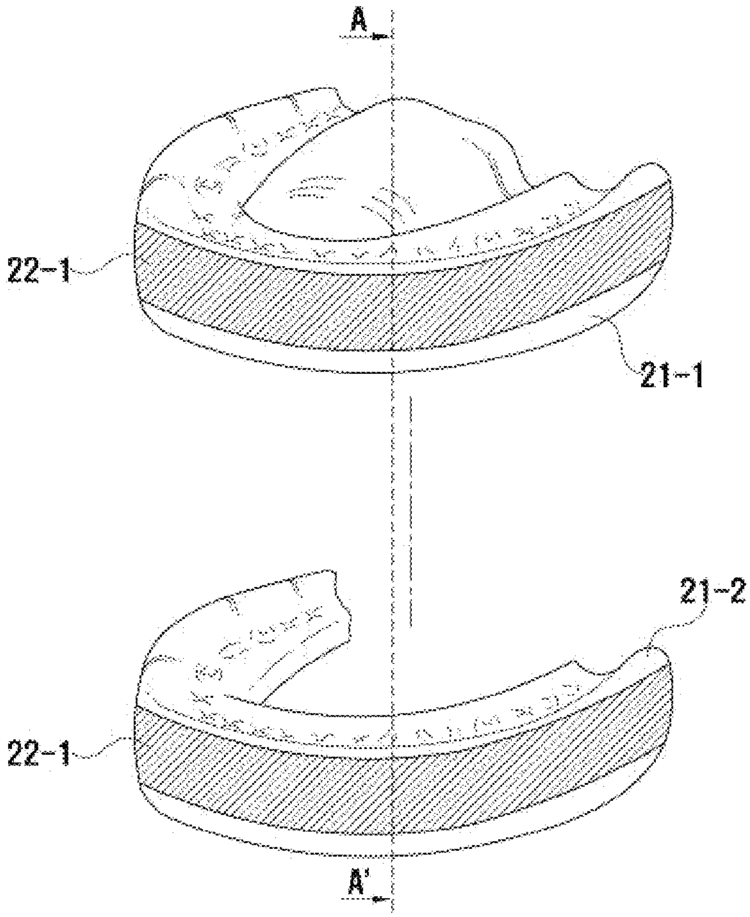
FIGS. 8A to 11B are views illustrating a mouthpiece of the inventive concept.
Figure 8B:
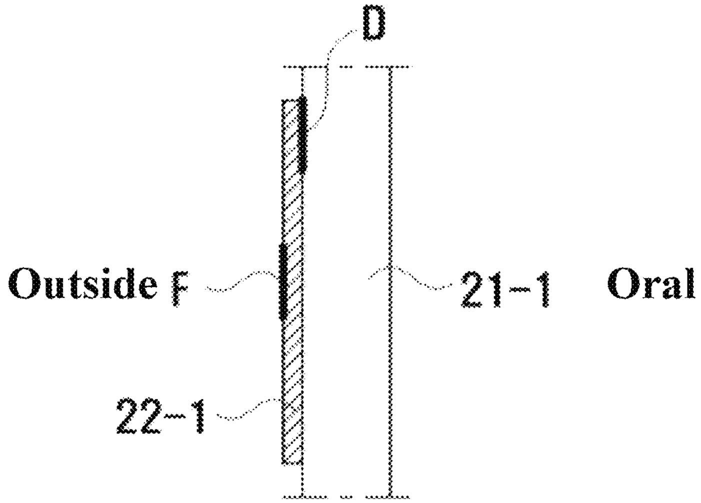
Figure 9A:
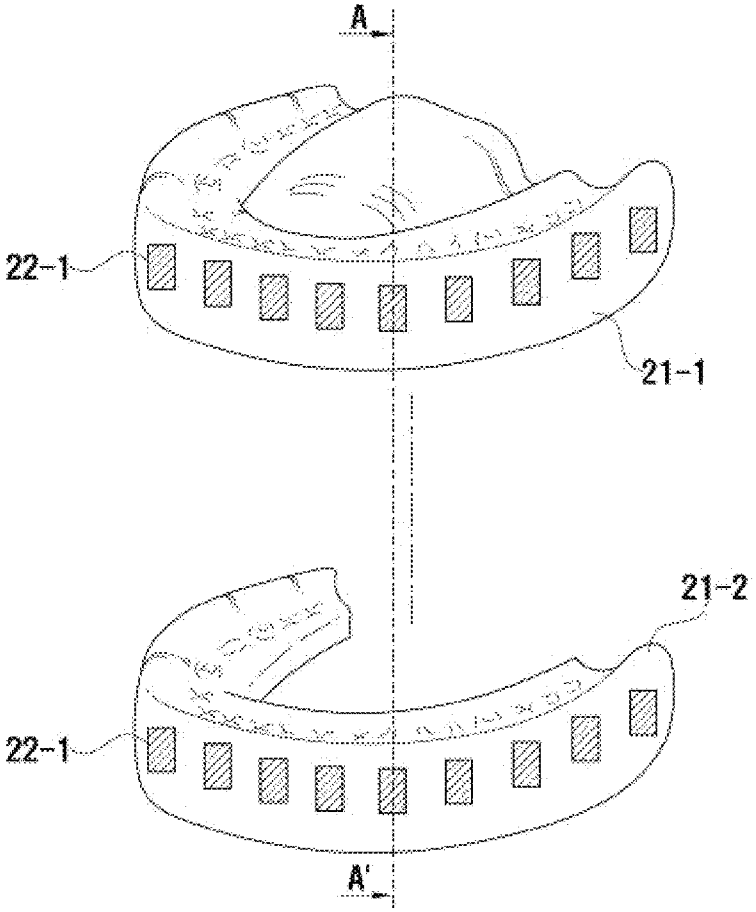
Figure 9B:
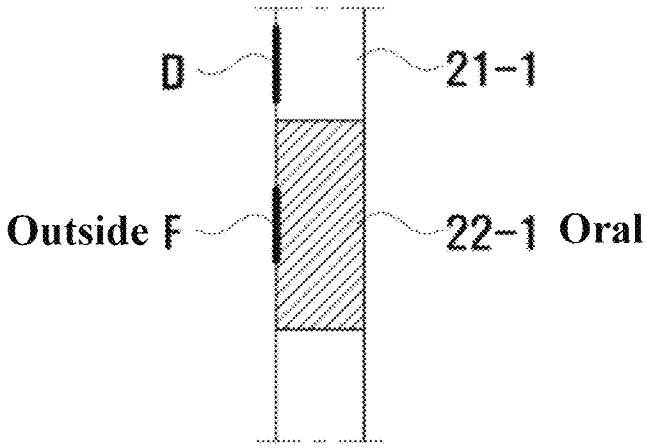
Figure 9C:
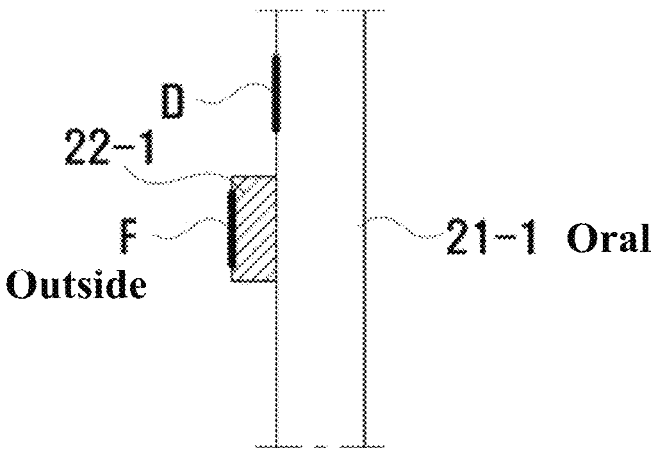
Figure 10A:
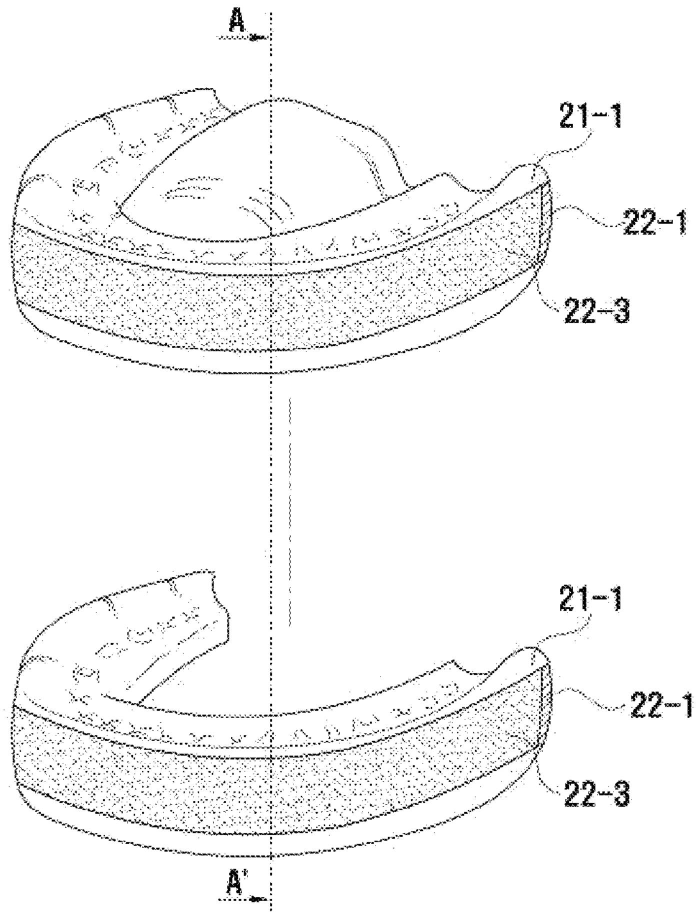
Figure 10B:
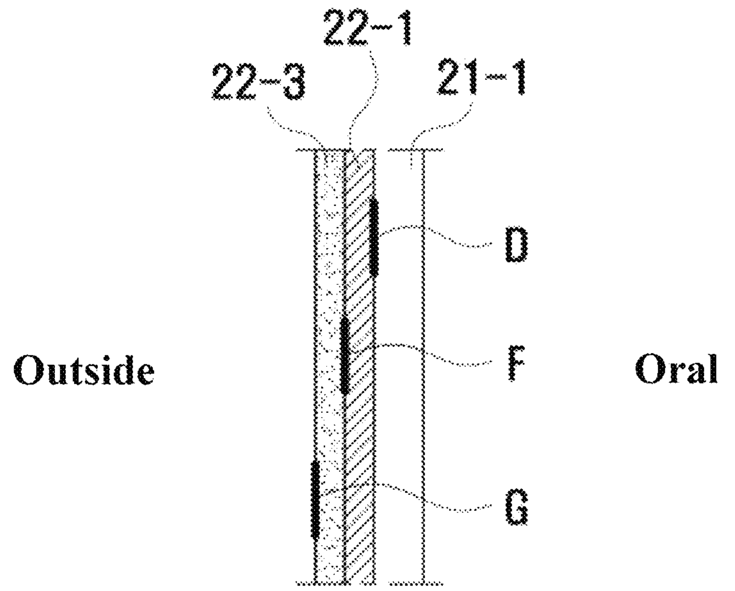
Figure 11A:
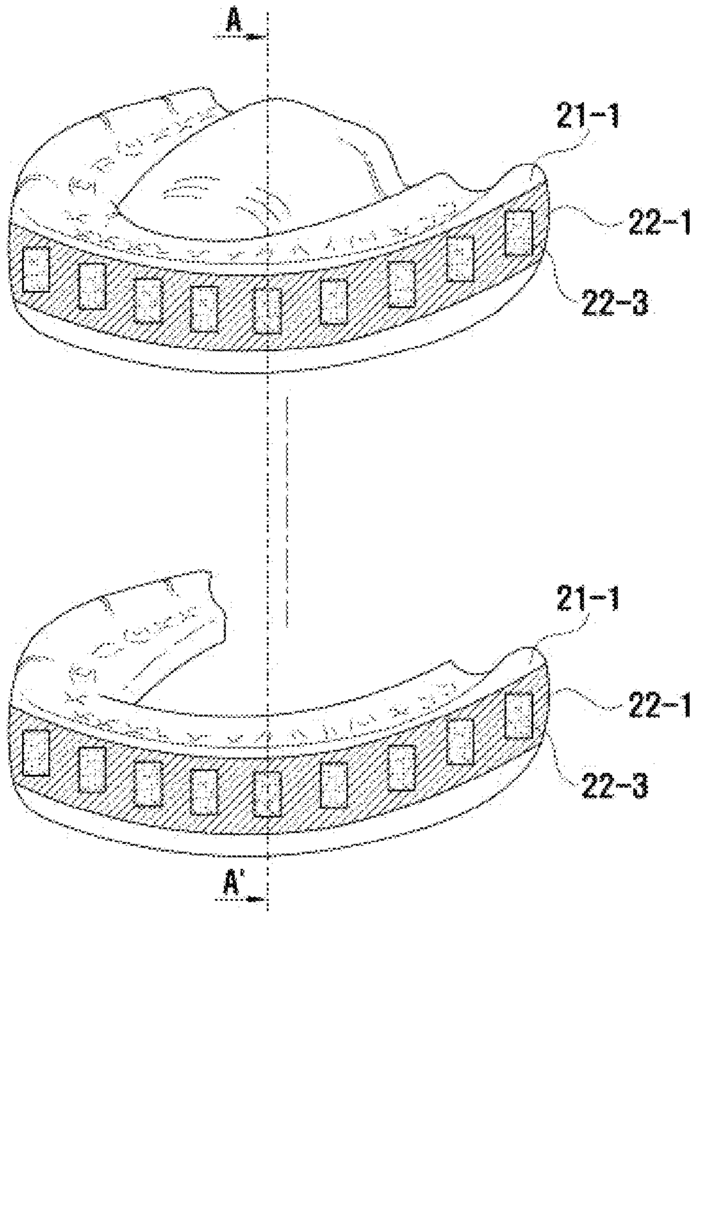
Figure 11B:
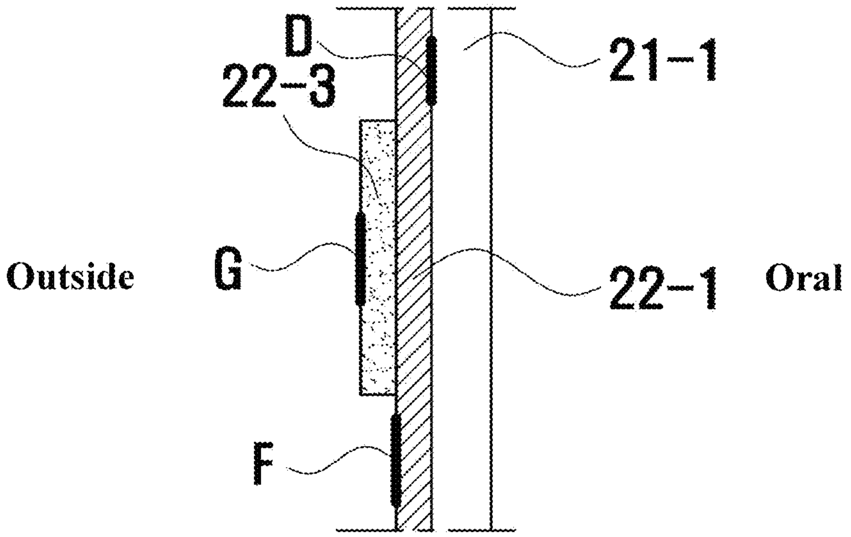
Figure 12:
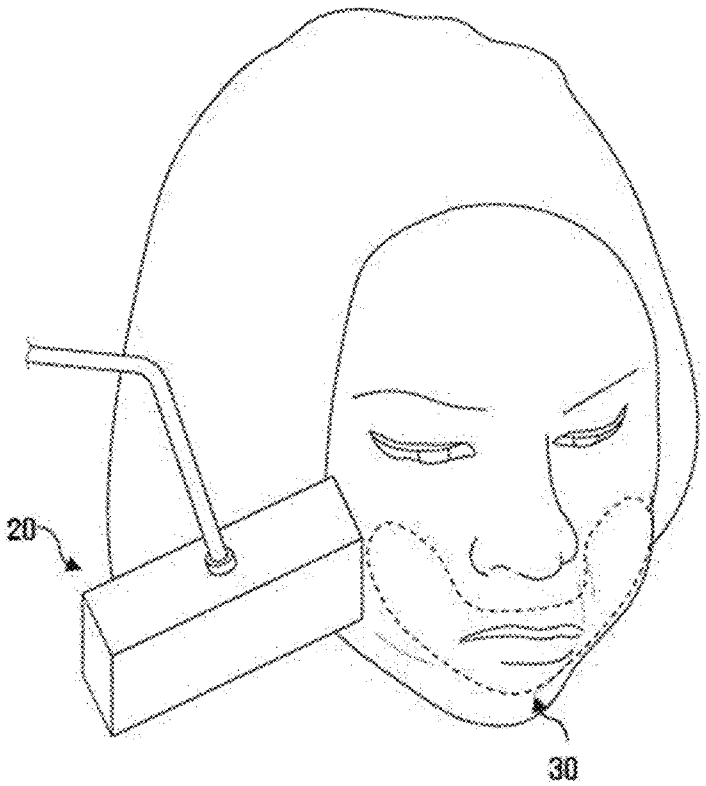
FIG. 12 is a conceptual view illustrating that a subject being treated with a skin treating apparatus of the inventive concept.

Hereinafter, a skin treating apparatus 100 of the inventive concept will be described with reference to the drawings. FIG. 5 is a conceptual view illustrating a skin treating apparatus of the inventive concept. FIGS. 6A and 6B are conceptual views illustrating various embodiments of a second electrode unit of the inventive concept. FIG. 7 is a conceptual view illustrating a cross-section and a system of a hand-piece of the inventive concept. FIGS. 8A to 11B are views illustrating a mouthpiece of the inventive concept. FIG. 12 is a conceptual view illustrating that a subject being treated with a skin treating apparatus of the inventive concept. Here, FIG. 8A is a perspective view of a mouthpiece according to an embodiment of the inventive concept. FIG. 8B is a cross-sectional view illustrated with respect to reference line A-A'. FIG. 9A is a perspective view of a mouthpiece according to another embodiment of the inventive concept. FIGS. 9B and 9C are cross-sectional views illustrated with respect to reference line A-A'. FIG. 10A is a perspective view of a mouthpiece according to yet another embodiment of the inventive concept. FIG. 10B is a cross-sectional view illustrated with respect to reference line A-A'. FIG. 11A is a perspective view of a mouthpiece according to yet another embodiment of the inventive concept. FIG. 11B is a cross-sectional view illustrated with respect to reference line A-A'.

The skin treating apparatus 100 of the inventive concept may include an electric power source unit 10, a mouthpiece 20, and a hand-piece 30. Furthermore, the skin treating apparatus 100 of the inventive concept may further include a pump 40 that additionally injects cooling water or a liquid chemical into the hand-piece 30.

The electric power source unit 10 may be electrically connected to the mouthpiece 20 and the hand-piece 30. A control module (not illustrated) may be embedded in the electric power source unit 10, and may control a wavelength band, an intensity, a direction, and the like of a power supply applied to a first electrode unit 22 of the mouthpiece 20 and a second electrode unit 32 of the hand-piece 30.

As an example, the electric power source unit 10 may apply an alternating current of a wavelength band of a high frequency to a first electrode 22-1 of the first electrode unit 22 and a second electrode 32-1 of the second electrode unit 32. In this case, referring to FIG. 3, an alternating current flows in the first electrode 22-1 and the second electrode 32-1 while changing a direction according to the cycle, and in particular, an electrical passage, in which an alternating current flows along several strands branched from a central strand of a retaining ligament when the alternating current flows from an inner side to an outer side and is spread out from a deep skin portion, may be generated.

Meanwhile, a display panel 11 may be provided in the electric power source unit 10. A medical doctor may be provided with various pieces of information that are necessary for treatment of skin through the display panel 11. As an example, the display panel 11 may display an intensity, a wavelength, a direction, and the like of the alternating current of the currently applied high frequency wavelength band. Furthermore, biometric information of the deep skin portion of a skin tissue or the like may be displayed.

Moreover, a manipulation unit 12 may be provided in the electric power source unit 10. A medical doctor may manipulate such that the skin treating apparatus 100 of the inventive concept is operated in a specific mode, through the manipulation unit 12. As an example, the medical doctor may control an intensity, a wavelength, a direction, and the like of the alternating current of the currently applied high frequency wavelength band, through the manipulation unit 12. Meanwhile, the manipulation unit 12 may be provided in a form of a touchscreen, and the medical doctor may perform manipulation by touching an image icon or the like of the manipulation unit 12.

The mouthpiece 20 may be inserted into an oral cavity of a patient (user) when skin is treated. The mouthpiece 20 may include an impression body 21 and the first electrode unit 22.

The impression body 21 may be a member that is disposed in the oral cavity of the patient and forms an external appearance of the mouthpiece 20. A material of the impression body 21 may be nonconductive, and accordingly, may prevent electrical energy of a high frequency from flowing in a tooth implant of the patient when the skin is treated.

The impression body 21 may be manufactured through an impression taking process, and the impression body 21 may have an external appearance corresponding to the oral cavity structure (including a tooth structure) of the patient, and in particular, engravings corresponding to the structure of the teeth of the patient may be formed in the impression body 21.

Because the oral cavity structures of the patients may be personally different, the patients wear a mouthpiece that does not correspond to the structure of his or her oral cavity structure when the mouthpieces are mass-produced in a specific shape. Accordingly, retaining ligaments, blood vessels, and inter-cell fiber tissues that are targets may not be smoothly used as the electrical passage as the first electrode 22-1 may deviate from a medically designed correct location.

Unlike this, because the mouthpiece 20 of the inventive concept uses the impression body 21 manufactured through the impression taking, the patient may wear the mouthpiece 20 corresponding to the structure of his or her oral cavity, and accordingly, the first electrode 22-1 may apply electrical energy of a high frequency to the medically designed correct location. As a result, when the mouthpiece 20 of the inventive concept is used, electrical energy of a high frequency may be accurately applied to the retaining ligament, the blood vessel, and the inter-cell fiber tissue that are targets.

Meanwhile, the impression body 21 may be manufactured through traditional impression captured using a bite tray, and may be manufactured through digital impression taking.

As an example, the impression body 21 may be manufactured by inserting the tray, in which an impression material (alginate, addition polymerization type silicon, or the like) is disposed, into the oral cavity of the patient, and biting the tray by the patient, and forming the impression material in correspondence of the oral cavity structure of the patient (a traditional impression taking method).

Unlike this, the impression body 21 may be manufactured by acquiring depth information (for example, three-dimensional depth information) on the oral cavity structure of a patient with a scanner and forming the impression body according to the depth information. In this case, various methods may be applied to the impression material forming method, and the impression body 21 may be manufactured by forming the impression material through three-dimensional printing (a digital impression taking method).

Meanwhile, the impression body 21 may include at least one of an upper jaw impression body 21-1 corresponding to at least a portion of an oral cavity structure of an upper jaw of the patient, and a lower jaw impression body 21-2 corresponding to at least a portion of an oral cavity structure of a lower jaw of the patient.

That is, for the impression body 21 of the inventive concept, only the upper jaw impression body 21-1 may be used and the lower jaw impression body 21-2 may be used according to the purpose of the treatment of the patient, and both of the upper jaw impression body 21-1 and the lower jaw impression body 21-2 may be used.

Meanwhile, when both of the upper jaw impression body 21-1 and the lower jaw impression body 21-2 are used, the first electrode 22-1 may only be disposed in the upper jaw impression body 21-1, may be disposed only in the lower jaw impression body 21-2, and may be disposed in both of the upper jaw impression body 21-1 and the lower jaw impression body 21-2.

Meanwhile, the upper impression body 21-1, as illustrated in FIGS. 8A, 9A, 10A, and 11A, may not be formed to correspond to the entire oral cavity structure of the upper jaw of the patient, but may be formed to correspond to a portion of the oral cavity structure of the upper jaw of the patient (as an example, may be formed to correspond to a right molar portion or a left molar portion, or may be formed to correspond to incisor teeth and canine teeth). Similarly, the lower jaw impression body 21-2 may not be formed to correspond to the entire oral cavity structure of the lower jaw of the patient, but may be formed to correspond to a portion of the oral cavity structure of the lower jaw of the patient (as an example, may be formed to correspond to a right molar portion, may be formed to correspond to a left molar portion, or may be formed to correspond to incisor teeth and canine teeth.

The first electrode unit 22 may be disposed in the impression body 21, and may electrically interact with the second electrode unit 32 disposed outside the oral cavity of the patient according to a potential difference (a voltage difference). The first electrode unit 22 may include the first electrode 22-1 and a conductive line 22-2.

The first electrode 22-1 may be a "ground terminal," and may be disposed in the impression body 21. That is, the alternating current of the wavelength band of the high frequency emitted from the second electrode 32-1 may be fed back in the first electrode 22-1.

The first electrode 22-1 may be bonded to and disposed on a surface of the impression body 21, and at least a portion of the first electrode 22-1 may be inserted into and disposed in an interior of the impression body 21 such that a portion thereof is exposed externally. That is, the first electrode 22-1 may be bonded to the surface of the completely manufactured impression body 21. Unlike this, the first electrode 22-1 may be coupled to the impression body 21 in the impression taking process. As an example, the first electrode 22-1 may be disposed in the tray together with the impression material, may be coupled to the impression material in a process of forming the impression material by the patient biting the tray (a process of the impression material being hardened and solidified), and may be disposed to be inserted into the interior of the completely manufactured impression body 21 (similar to insert injection molding).

For example, the first electrode 22-1 is a single member, and as illustrated in FIGS. 8A and 8B, a large area may be formed and disposed on an outer surface "D" of the impression body 21. That is, referring to FIG. 8B, an outer surface "F" of the first electrode 22-1 may continuously protrude from the outer surface "D" of the impression body 21 and may be integrally formed with and disposed on the outer surface "D" of the impression body 21. In this case, because an active area of the first electrode 22-1 is wide, electrical energy may be prevented from being concentrated in a specific fine part of the face of the patient (for reference, the user may feel a burning sensation or pain when the electrical energy is concentrated.) Accordingly, the first electrode 22-1 may cover 95% or more of a front surface of the impression body 21, but the inventive concept is not limited thereto.

Figure 3:
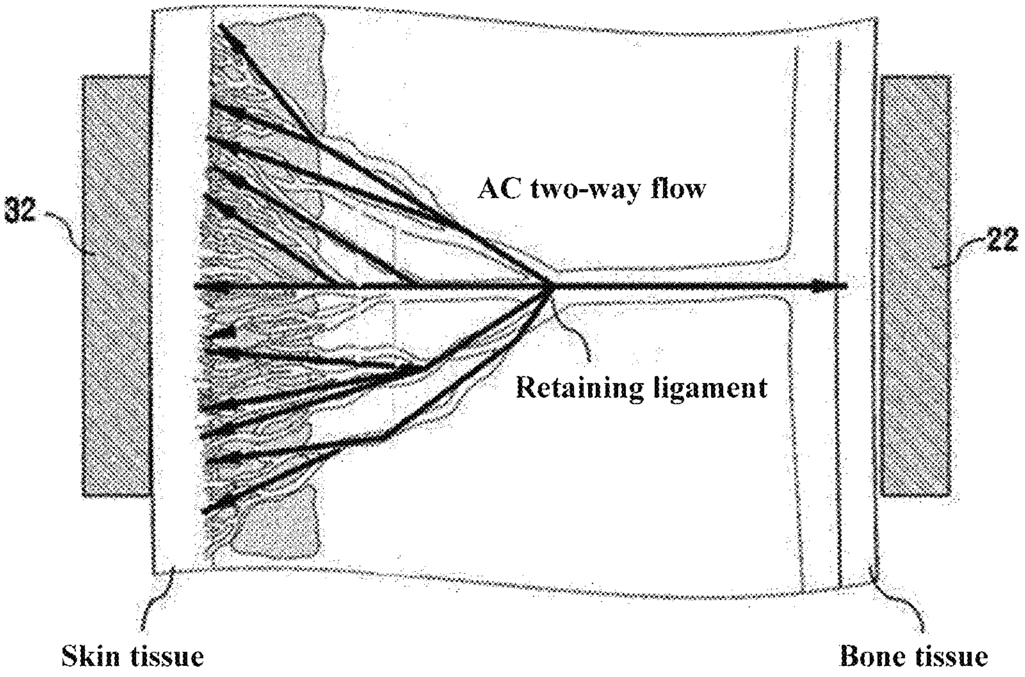
FIG. 3 is a conceptual view illustrating an alternating current flows through a facial retaining ligament during treatment of skin using a skin treating apparatus according to the inventive concept.
Figure 4:
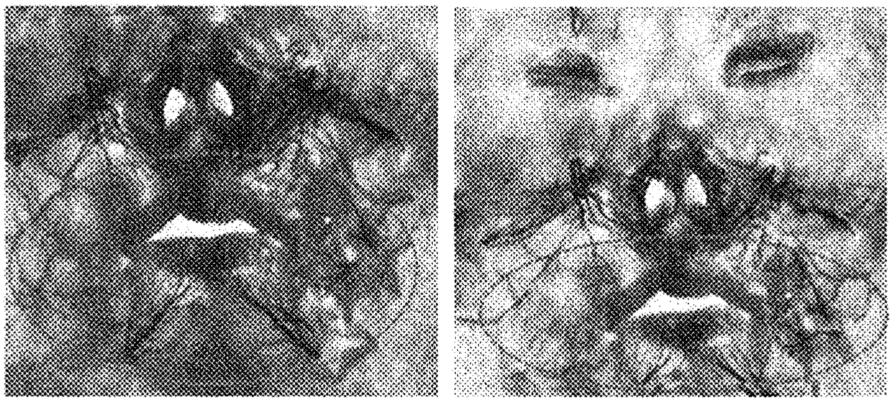
FIG. 4 is a conceptual view viewed from an interior of the face of a human body, and illustrating that inner mucous membranes and nerves are distributed in a surface form while forming a net.

Here, because the first electrode 22-1 becomes a large area, it may cover all of the retaining ligaments, the blood vessels, and the inter-cell fiber tissues illustrated in FIGS. 3 and 4 and is adapted to be utilized as an electrical passage.

Then, the first electrode 22-1 disposed to protrude from the outer surface "D" of the impression body 21 may have a thickness that the user does not feel foreign body sensations when it is inserted into the interior of the oral cavity of the user while being coupled to the impression body 21.

According to the embodiment, the first electrode 22-1, as illustrated in FIGS. 9A and 9B, may include a plurality of electrode segments that are spaced apart from each other. That is, referring to FIG. 9B, a portion of the first electrode 22-1 may be inserted into the interior of the impression body 21 and may be formed such that the outer surface "F" of the first electrode 22-1 is exposed externally. Here, a plurality of first electrodes 22-1 are disposed to be arranged in one direction, the inventive concept is not limited thereto, but the plurality of first electrodes 22-1 may be arranged in various methods.

Accordingly, the outer surface "F" that is an exposed surface of the first electrode 22-1 and the outer surface "D" of the impression body 21 may be located on the same line. Then, the first electrode 22-1 discontinuously disposed in the interior of the impression body 21 may have the same thickness as that of the impression body 21, but the inventive concept is not limited thereto.

According to the embodiment, the first electrode 22-1 may be continuously disposed from the outer surface "D" of the impression body 21 such that a portion thereof is exposed externally. That is, referring to FIG. 9C, the outer surface "F" of the first electrode 22-1 may discontinuously protrude from the outer surface "D" of the impression body 21 and be disposed thereon. Then, the first electrode 22-1 disposed to protrude from the outer surface "D" of the impression body 21 may have a thickness that the user does not feel foreign body sensations when it is inserted into the interior of the oral cavity of the user while being coupled to the impression body 21.

According to the embodiment, the first electrode unit 22, as illustrated in FIGS. 10A and 10B, may include an insulation layer 22-3 disposed to correspond to the outer surface "F" that is the exposed surface of the first electrode 22-1. That is, the exposed surface of the first electrode 22-1 may be covered to be sealed by the insulation layer 22-3.

For example, the insulation layer 22-3 may be disposed on the outer surface "F" of the first electrode 22-1 disposed on the surface "D" of the impression body 21 while forming the large area, to form a large area. That is, referring to FIG. 10B, an outer surface "G" of the insulation layer 22-3 may continuously protrude from the outer surface "F" of the first electrode 22-1 and may integrally formed with and disposed on the outer surface "F" of the first electrode 22-1.

In this way, because the insulation layer 22-3 is formed on the outer surface "F" of the first electrode 22-1, the electric currents of the electrical energy delivered to the deep skin portion of the patient directly flow to the mucous membrane of the oral cavity so that the insulation layer 22-3 may be utilized as an electrical passage. That is, because the insulation layer 22-3 functions as a ground for the electrical energy, the electrical energy may be smoothly delivered to the deep skin portion of the patient in an insulated state so that the user cannot feel burned or pain when the electrical energy is concentrated.

Figure 13:
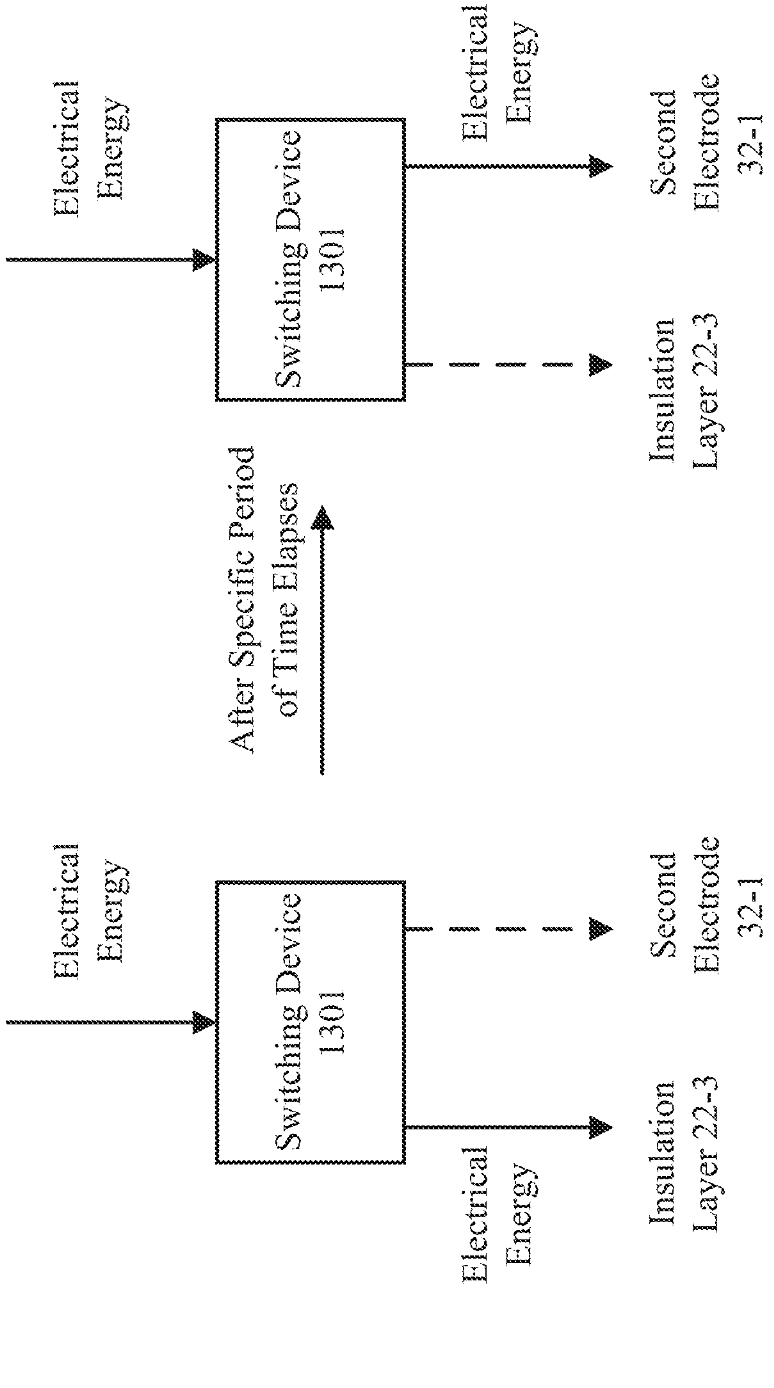
FIG. 13 depicts operation of a switching device.

According to the embodiment, when the electrical energy of the wavelength band of the high frequency having a high energy density is delivered to the deep skin portion, the electrical passage progressed by the insulation layer 22-3 may be delivered to the second electrode 32-1 and may deliver the electrical energy to the deep skin portion after a specific period of time elapses. For example, when 5 seconds elapses after the electrical energy is delivered, the electrical passage may be changed from the insulation layer 22-3 to the second electrode 32-1 using a separate switching device 1301 (see FIG. 13). Accordingly, a safety accident, such as a burn, which may be generated when the electrical energy is concentrated in the oral cavity mucous membrane due to a long-time treatment or a repeated treatment, may be minimized.

According to the embodiment, the insulation layer 22-3, as illustrated in FIGS. 11A and 11B, may include a plurality of electrode segments that are spaced apart from each other.

For example, the insulation layer 22-3 may be discontinuously disposed such that a portion of the outer surface "F" of the first electrode 22-1 disposed on the surface "D" of the impression body 21 while forming a large area is exposed externally. That is, referring to FIG. 11B, an outer surface "G" of the insulation layer 22-3 may discontinuously protrude from and be disposed on the outer surface "F" of the first electrode 22-1. Then, the insulation layer 22-3 disposed to protrude from the outer surface "F" of the first electrode 22-1 may have a thickness that the user does not feel foreign body sensations when it is inserted into the interior of the oral cavity of the user while being coupled to the impression body 21.

The insulation layer 22-3 is formed of an insulating material, and thus may not influence the first electrode unit 1 used as a ground terminal.

That is, because at least a portion of the first electrode unit 22 is protected by the insulation layer 22-3 while a treatment is made using the skin treating apparatus 100 that uses the electrical energy of the wavelength band of the high frequency having the high energy density as illustrated in FIG. 12 so that the user may more safely protected from a burn or pain. For example, even when the wavelength band of the high frequency is 10 MHz or more, the treatment may be made by electrically stimulating the skin with the insulation layer 22-3 safely.

In other words, because the insulation layer 22-3 is formed to surround and cover the surface of the first electrode 22-1 formed on the surface "D" of the impression body 21, the skin may be stimulated while not being damaged to perform the treatment safely even when high-frequency wave energy is irradiated in a noncontact state, in which the first electrode 22-1 is not in a complete contact in the oral cavity.

Meanwhile, the conductive line 22-2 of the first electrode unit 22 may electrically connect the first electrode 22-1 and the electric power source unit 10, and accordingly, the electric power source unit 10 may apply a high-frequency alternating current to the first electrode 22-1.

The hand-piece 30 may contact the skin of the patient while being gripped by a hand of the medical doctor. Because electrical energy may be generated between the hand-piece 30 and the mouthpiece 20 and heat is concentrated in the deep skin portion, the treatment of the skin may be performed. The hand-piece 30 may include a housing 31, the second electrode unit 32, a driving unit 33, and a support unit 34.

The housing 31 may be an external member that forms an external appearance of the hand-piece 30. The housing 31 may be manufactured through plastic injection-molding and the like. However, the inventive concept is not limited thereto, but the housing 31 may be formed of various materials. The second electrode unit 32, the driving unit 33, and the support unit 34 may be disposed in an interior of the housing 31. In this case, the second electrode unit 32 may be supported by the support unit 34, and may be disposed to move in a lengthwise direction (an upward/downward direction) thereof.

The housing 31 may include a first housing 31-1 and a second housing 31-2. The first housing 31-1 may be disposed on a lower side, and the second housing 31-2 may be disposed on an upper side. The first housing 31-1 and the second housing 31-2 may be screw-coupled to each other.

The second electrode unit 32 and the support unit 34 may be disposed in an interior of the first housing 31-1. To this end, a first chamber "a" and a second chamber "b" may be formed in the interior of the first housing 31-1. The first chamber "a" may be disposed on a lower side, and may be connected to an outside through a plurality of holes formed on a lower surface of the first housing 31-1. The second chamber "b" may be disposed on an upper side. Meanwhile, an upper surface of the second chamber "b" may have an opened part, and the opened part of the second chamber "b" may be closed by a lower surface of the second housing 31-2.

The second electrode unit 32 may be disposed in the first chamber "a" of the first housing 31-1, and the support unit 34 may be disposed in the second chamber "b" of the first housing 31-1. When the second electrode unit 32 is moved downwards, it may be exposed externally through a plurality of openings formed on a lower surface of the first housing 31-1. Meanwhile, an upper portion of the second electrode unit 32 may be disposed to be elastically supported by the support unit 34.

Moreover, when the pump 40 is added to the skin treating apparatus 100 of the inventive concept, various fluids may be injected into the first chamber "a" of the first housing 31-1. As an example, cooling water, a drug, and the like for alleviating rashes and heat emission of the skin may be injected into the first chamber "a".

The driving unit 33 may be disposed in an interior of the second housing 31-2. In this case, the driving unit 33 may be connected to the support unit 34 at a border of the first housing 31-1 and the second housing 31-2 to drive the second electrode unit 32.

The second electrode unit 32 may include the second electrode 32-1 and a conductive line 32-6.

The second electrode 32-1 may be a "power terminal." That is, the second electrode 32-1 may emit an alternating current of a wavelength band of a high frequency. Meanwhile, because the skin treating apparatus 100 of the inventive concept uses electrical energy of a wavelength band of a high frequency having a high energy density, damaged collagen and aged skin tissues may emit heat at a high temperature and improve a treatment effect (skin reproduction efficiency).

The second electrode 32-1 may include a plurality of needle electrodes. In this case, the second electrode 32-1 may be referred to as an "RF needle electrode." Hereinafter, it will be described as an example that the second electrode 32-1 includes a plurality of needle electrodes, but the form of the second electrode 32-1 of the inventive concept is not limited thereto.

As an example, as illustrated in FIG. 6A, the second electrode unit 32 may include a plurality of ball electrodes 32-3. In this case, the plurality of ball electrodes 32-3 may roll on a surface of skin. Furthermore, because the plurality of ball electrodes 32-3 do not require vertical driving, the driving unit 33 may be omitted.

Furthermore, as illustrated in FIG. 6B, the second electrode unit 32 may include a flat plate electrode 32-4 having a pattern. In this case, in order to form the pattern, an insulation layer 32-5 having an opened pattern part may be laminated on the flat plate electrode 32-4. Furthermore, because the flat plate electrode 32-4 does not require vertical driving, the driving unit 33 may be omitted.

The second electrode unit 32 may be disposed in the interior of the housing 31 to reciprocate in a lengthwise direction (upward/downward direction) thereof. To this end, an upper end of the second electrode unit 32 may be connected to a support pad 34-2 of the support unit 34 and may be elastically supported in the lengthwise direction (upward/downward direction) thereof. A lower end of the second electrode unit 32 may be a tip end to pass through the epidermis of the skin. Accordingly, the tip end of the second electrode unit 32 may be disposed to face the first electrode unit 22 while the mucous membrane of the oral cavity being interposed therebetween. Accordingly, when the second electrode unit 32 is moved downwards, electrical energy may be applied to the dermis of the deep skin portion. Meanwhile, a depth of the deep skin portion, to which the electrical energy is applied, may be determined according to a stroke of the second electrode unit 32. The second electrode unit 32 may be moved upwards to return after the electrical energy is applied to the dermis of the deep skin portion. According to the embodiment, the second electrode unit 32 may apply the electrical energy to the surface of the skin.

Each of the plurality of needles may have a needle shape that extends upwards and downwards and forms a length thereof. A lower end of each of the plurality of needle electrodes may be a tip end.

Referring to FIG. 5, the plurality of needle electrodes may be arranged to form columns and rows on a plane that is perpendicular to the lengthwise direction. Accordingly, the plurality of needle electrodes may equally cover a wide range. Then, the plurality of needle electrodes may be sufficiently sharp to pass through the epidermis of the skin, but may be rounded.

Meanwhile, the conductive line 32-6 of the second electrode unit 32 may electrically connect the second electrode 32-1 and the electric power source unit 10, and accordingly, the electric power source unit 10 may apply a high-frequency alternating current to the second electrode 32-1.

The driving unit 33 may drive the second electrode 32-1 in the lengthwise direction (upward/downward direction). The driving unit 33 may employ various kinds of devices. As an example, the driving unit 33 may be a "step motor". However, the inventive concept is not limited thereto, but as an example, the driving unit 33 may be a "hydraulic or pneumatic cylinder."

The driving unit 33 may include a rod 33-1. The rod 33-1 may be connected to the support pad 34-2 of the support unit 34, and may deliver an upward/downward driving force generated by the driving unit 33 to the support pad 34-2.

The support unit 34 may elastically support the second electrode 32-1 upwards and downwards. Moreover, the support unit 34 may receive the driving force of the driving unit 33 and operate the second electrode 32-1. The support unit 34 may include an elastic member 34-1 and the support pad 34-2.

The elastic member 34-1 of the support unit 34 may be a "three-dimensional spiral spring." An upper end of the elastic member 34-1 may contact the support pad 34-2, and a lower end of the elastic member 34-1 may contact a bottom surface of the second chamber "b" of the first housing 32-1. Accordingly, the elastic member 34-1 may elastically support the support pad 34-2 upwards and downwards. Meanwhile, as described above, the support pad 34-2 may be connected (coupled) to the upper end of the second electrode 32-1. As a result, the second electrode 32-1 may be elastically supported upwards and downwards by the support unit 34.

Figure 14:
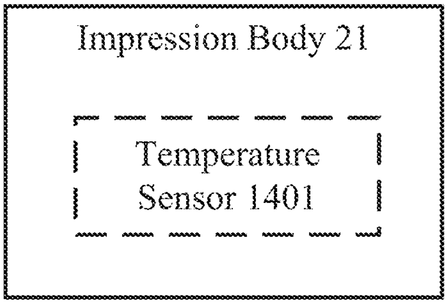
FIG. 14 depicts a temperature sensor.

According to the embodiment, the mouthpiece 20 may include a temperature sensor 1401 (see FIG. 14) that is provided on an inner surface of the impression body 21 that contacts the skin of the user and detects a temperature change between the impression body 21 and the mucous membrane of the oral cavity.

For example, the skin of the user may be prevented from being damaged due to an excessive temperature rise between the impression body 21 and the mucous membrane of the oral cavity in advance by detecting the temperature rise, and accordingly, the user may safely use the mouthpiece 20.

Here, the temperature sensor may be inserted into the interior of the impression body 21, but the inventive concept is not limited thereto and may be formed at a location, at which a temperature change between the oral cavity of the user and the impression body 21 may be detected. For example, the temperature sensor may be located between the impression body 21 and the insulation layer 22-3 or between the impression body 21 and the first electrode 22-1.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A mouthpiece for treating skin, comprising:

an impression body configured to be disposed in an oral cavity of a patient, wherein the impression body has a shape corresponding to a structure of the oral cavity of the patient; and a first electrode on an outer surface of the impression body and forming a ground terminal configured to receive an alternating current (AC) emission from a second electrode disposed outside the oral cavity of the patient, wherein the first electrode is a continuous electrode member extending across an entirety of a front portion of the impression body corresponding to a front of the oral cavity.

2. The mouthpiece of claim 1, wherein the impression body comprises impression material which was shaped based on the patient having bitten down on a tray comprising the impression material.

3. The mouthpiece of claim 1, wherein the impression body comprises impression material which was shaped based on having acquired depth information regarding the structure of the oral cavity of the patient with a scanner.

4. The mouthpiece of claim 1, wherein the first electrode spans an entire width of the impression body.

5. The mouthpiece of claim 1, wherein the first electrode covers at least 95% of the outer surface of the impression body.

6. The mouthpiece of claim 1, wherein the first electrode extends across a first side portion of the impression body corresponding to a first side of the oral cavity.

7. The mouthpiece of claim 6, wherein the first electrode extends across a second side portion of the impression body corresponding to a second side of the oral cavity.

8. A skin treatment system, comprising:

a mouthpiece configured to be disposed in an oral cavity of a patient, wherein the mouthpiece comprises a first electrode and an impression body, wherein the first electrode is a ground electrode the first electrode is a continuous electrode member extending across an entirety of a front portion of the impression body corresponding to a front of the oral cavity; and a handpiece configured to apply electrical energy to a skin portion of the patient disposed outside the oral cavity of the patient via one or more second electrodes, wherein a pathway for the applied electrical energy includes the electrical energy being emitted via the one or more second electrodes and fed back through the first electrode.

9. The system of claim 8, wherein the first electrode is disposed on an outer surface of the impression body.

10. The system of claim 8, wherein the first electrode is partially disposed in an interior of the impression body and partially exposed.

11. The system of claim 10, wherein the exposed surface of the first electrode and an outer surface of the impression body are coplanar.

12. The system of claim 8, further comprising:

a switching device configured to switch between delivery of the electrical energy to the one or more second electrodes and delivery of the electrical energy to an insulation layer disposed on a surface of the first electrode.

13. The system of claim 8, further comprising:

a temperature sensor configured to detect a change in temperature corresponding to the oral cavity.

14. The system of claim 8, wherein the first electrode spans an entire width of the impression body.

15. The system of claim 8, wherein the first electrode covers at least 95% of the outer surface of the impression body.

16. The system of claim 8, wherein the first electrode further extends across a first side portion of the impression body corresponding to a first side of the oral cavity.

17. The system of claim 16, wherein the first electrode further extends across a second side portion of the impression body corresponding to a second side of the oral cavity.

* * * * *